United States Patent [19]

Denny

[11] 4,066,661

[45] Jan. 3, 1978

[54] PROCESS FOR THE PREPARATION OF SUBSTITUTED TRICHLOROACETAMIDINE DERIVATIVES

[75] Inventor: George H. Denny, Lansdale, Pa.

[73] Assignee: Merck & Co., Inc., Rahway, N.J.

[21] Appl. No.: 691,759

[22] Filed: June 1, 1976

[51] Int. Cl.$^2$ ............................................ C07D 209/14
[52] U.S. Cl. ................................ 260/326.15; 560/252
[58] Field of Search ..................................... 260/326.15

[56] References Cited

U.S. PATENT DOCUMENTS 2,855,398  10/1958  Voegtli ............................ 260/326.15

OTHER PUBLICATIONS

Gautier et al, The Chemistry of Amidines and Imidates, 1975, John Wiley & Sons, pp. 296–297, pertinent.
Sandler and Karo, Organic Functional Group Preparations, vol. III (1972) Academic Press, p. 227 pertinent.

Primary Examiner—Ethel G. Love
Attorney, Agent, or Firm—David L. Rose; J. Jerome Behan

[57] ABSTRACT

Substituted trichloroacetamidine derivatives are prepared by treating an appropriately substituted imidate with ammonia. The imidate intermediates are prepared by treating an appropriately substituted amine with an imidating reagent.

9 Claims, No Drawings

PROCESS FOR THE PREPARATION OF SUBSTITUTED TRICHLOROACETAMIDINE DERIVATIVES

SUMMARY OF THE INVENTION

This invention is related to a novel process for the preparation of certain trichloroacetamidine derivatives. Specifically this process is concerned with the reaction of an appropriately substituted imidate with ammonia. Thus, it is an object of this invention to describe the preparation of said trichloroacetamidine compounds. It is a further object of this invention to describe the preparation of the imidate intermediates from known starting materials and imidating reagents. Further objects will become apparent from a reading of the following description of the invention.

DESCRIPTION OF THE INVENTION

N-(3-indolylmethyl) trichloroacetamidine and N-(2-acetoxy-3-phenoxypropyl) trichloroacetamidine and potent cardiotonic agents. A cardiotonic agent stimulates the contractile force of the heart muscle, and thus increases the cardiac output. A cardiotonic agent is required for the treatment of congestive heart failure which results when the heart pumps less blood than is required by the metabolic demands of the body. The objective of treatment of congestive heart failure is to restore the balance of supply and demand for blood. This can be achieved through the instant cardiotonic agents which improve myocardial contractility and influence cardiac output to meet the demands of the body.

The above compounds are prepared by treating an appropriately substituted imidate with ammonia as seen in the following reaction scheme:

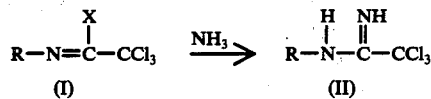

wherein R is 3-indolylmethyl or 2-acetoxy-3-phenoxy propyl; and X is a halogen, preferably chloro, or lower alkoxy, preferably methoxy or ethoxy.

The reaction is carried out preferably with ammonia dissolved in a solvent such as water or a loweralkanol. Liquid ammonia may also be employed, however. It is preferred to use an excess of ammonia to insure the completion of the reaction although a single molar equivalent of ammonia reacts with the imidate.

Further excess ammonia may be required where X is a halogen. In such cases a hydrohalic acid is liberated during the course of the reaction. It is preferred to neutralize this acid in order to facilitate the isolation of the product. This may be accomplished by using excess ammonia or by including in the reaction mixture a tertiary amine such as pyridine or a triloweralkylamine.

Generally the imidate is also dissolved in an inert solvent such as a hydrocarbon, chlorinated hydrocarbon, ether, alcohol, dimethyl formamide, dimethyl sulfoxide, hexamethylphosphoramide and the like. If desired, however, the imidate may be added directly to the ammonia solution or liquid ammonia.

The reaction is generally complete in from 5 to 1 week at from room temperature to about 100° C., lower temperature requiring a longer reaction time. Longer reaction times may be required for the lower temperature ranges or if the starting material is of limited solubility in the reaction solvent. The product is isolated by techniques known to those skilled in this art.

Since the products of the instant invention are basic compounds, it is possible, and may be desirable to isolate such products in the form of the acid addition salt. The mineral acid salts such as hydrohalide, hydrochloride, nitrate, sulfate and the like are preferred. They are prepared from the free base, and the free base is liberated therefrom by procedures known to those skilled in the art.

The imidate starting materials are prepared by different procedures depending upon the nature of X. When X is a loweralkoxy group the imidate is prepared in one process by treating 3-amino methyl indole or 2-acetoxy-3-phenoxy propylamine with triloweralkyl orthotrichloroacetate. The trimethyl compound is preferred. The reaction is preferably carried out in a solvent. Any solvent capable of dissolving the starting materials without interfering with the reaction is acceptable. Loweralkanols, hydrocarbons, chlorinated hydrocarbons, ethers, and other polar and non-polar solvents are acceptable. The reaction is carried out preferably at room temperature although temperatures up to the reflux temperature of the reaction mixture are acceptable. The reaction is complete in from 10 minutes to 3 hours. The imidate is isolated by procedures known to those skilled in this art.

The starting material imidates wherein X is loweralkoxy or halogen may be prepared by treating 3-aminomethylindole or 2-acetoxy-3-phenoxypropylamine with a trichloroacetyl acylating agent such as a trichloro acetyl halide, and treating the resultant trichloroacetamide derivative with an imidating reagent as shown in the following reaction scheme:

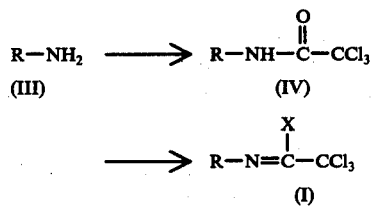

wherein R and X are as previously defined.

The acylation is carried out preferably with trichloroacetyl chloride in an inert, aprotic solvent such as a hydrocarbon, chlorinated hydrocarbon, an ether, and the like. The reaction is complete in from 5 minutes to 1 hour at from room temperature to the reflux temperature of the reaction mixture. The reaction may be somewhat exothermic in its initial stages. Thus, the initial combination of the reagents may be carried out at the lower temperature ranges, or by adding the acylating reagent to the amine in a dropwise manner. Generally addition periods of from 1 to 5 minutes are adequate, although large scale reactions may utilize even longer addition periods.

The trichloroacetamide compound (IV) is then treated with an imidating agent to produce the imidate starting material (I). The imidating agent of choice to produce the imidate wherein X is loweralkoxy in a triloweralkyloxonium tetrafluoroborate. The reaction is carried out at approximately room temperature for from 1 to 24 hours. It is preferred to use a solvent to dissolve the reacting materials. A hydrocarbon or halogenated hydrocarbon, such as benzene, toluene, hexane, methylene chloride, chloroform, carbon tetrachloride and the like are preferred.

The imidating agent of choice to produce the imidate wherein X is halogen is a phosphorous pentahalide. Phosphorous pentachloride is preferred in order to prepare the imidate wherein X is chloride. The reaction is carried out preferably in the absence of a solvent at an elevated temperature. At about 100° to 125° C. the reaction is generally complete in about 2 to 6 hours. The completion of the reaction is more accurately determined, however, by observing when the liberation of hydrogen halide gas has ended. Since the hydrogen halide gas is liberated during the course of the reaction, when such liberation ceases is an accurate determinant of the end of the reaction.

The imidate may be treated with ammonia directly to produce the trichloroacetamidine (II) or it may be purified prior to such reaction.

The following examples are provided in order to aid in the understanding of this invention. They are not to be construed as limitative of the invention.

EXAMPLE 1

N-(3-Indolylmethyl) trichloroacetamidine

To a stirred solution of 14.6 g. (0.1 mole) of 3-(aminomethyl) indole in 30 ml. of benzene is added dropwise 18.2 g. (0.1 mole) of trichloroacetyl chloride over a period of approximately 5 minutes. The reaction mixture is heated at reflux for 30 minutes, cooled and concentrated to dryness in vacuo. The resultant solid is broken up and ground in a mortar to give a powder which is mixed well with 20.8 g. (0.1 mole) of phosphorus pentachloride. The mixture is heated in an oil bath at 110° C. until the evolution of hydrogen chloride ceases (approximately 3 hours). The reaction mixture containing the imidoyl chloride is cooled to room temperature and dry pyridine (7.9 g., 0.1 mole) is added followed by 6.5 ml. of concentrated aqueous ammonia. The reaction mixture is then stirred and warmed to 90° C. for 30 minutes, after which 100 ml. of water is added dropwise to precipitate the product. Overnight storage in the cold affords a solid which is crystallized from benzene-hexane to provide N-(3-indolylmethyl) trichloroacetamidine m.p. 135.5° to 138.5° C.

EXAMPLE 2

N-(2-Acetoxy-3-phenoxypropyl) trichloroacetamidine hydrochloride

To a solution of 10.4 g. (0.05 mole) of 2-acetoxy-3-phenoxypropylamine in 30 ml. of benzene is added dropwise 9.1 g. (0.05 mole) of trichloroacetyl chloride. The reaction mixture is heated at reflux for 30 minutes, cooled and concentrated to dryness in vacuo. The solid residue is suspended in 100 ml. of dry methylene chloride and to it is added a solution of 9.45 g. (0.05 mole) of triethyloxonium tetrafluoroborate in 25 ml. of dry methylene chloride. The clear solution obtained after stirring overnight at room temperature is concentrated under vacuum to 40 ml. and diluted with 200 ml. of ether, causing the imidate tetrafluoroborate to precipitate. This is collected, redissolved in 125 ml. of methylene chloride and treated with a solution of 1.5 g. of ammonia in 160 ml. of absolute ethanol. The reaction is allowed to stand for 3 days, then concentrated to dryness, treated with 50 ml. of water, made basic with 5N sodium hydroxide, and extracted into ether. Concentration under reduced pressure gives the crude free base, which is dissolved in benzene and treated with ethanolic hydrogen chloride affording N-(2-acetoxy-3-phenoxypropyl)trichloroacetamidine hydrochloride m.p. 70° to 77° C.

EXAMPLE 3

N-(3-Indolylmethyl)trichloroacetamidine

A solution of 13.2 g. (0.1 mole) or 3-(aminomethyl)-indole in 200 ml. of methanol is combined with 22.3 g. (0.1 mole) of trimethyl orthotrichloroacetate. After 30 minutes at room temperature, the reaction mixture is concentrated to dryness in vacuo to give the imidate. This is dissolved in benzene and treated with excess ethanolic ammonia. After standing for 3 hours at room temperature, the solvents are removed in vacuo and the residue taken up in chloroform, washed with water, dried over magnesium sulfate, filtered and concentrated to dryness, in vacuo. Recrystallization from benzene-hexane gives N-(3-indolymethyl) trichloroacetamidine m.p. 135.5° to 138.5° C.

What is claimed is:

1. A process for the preparation of a compound having the formula

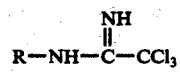

wherein R is 3-indolylmethyl, which comprises treating a compound having the formula:

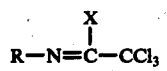

wherein R is as previously defined and X is loweralkoxy or halogen, with ammonia at a temperature of from room temperature to 100° C for a period of from 5 minutes to 1 week.

2. The process of claim 1 wherein X is methoxy, ethoxy or chlorine.

3. A process for the preparation of a compound having the formula:

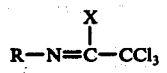

wherein R is 3-indolylmethyl, and X is loweralkoxy or halogen, which comprises treating a compound having the formula:

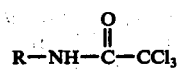

wherein R is as previously defined, with an imidating agent selected from triloweralkyloxonum tetrafluoroborate, at about room temperature for from 1 to 24 hours or phosphorous pentahalide at about 100° to 125° C for from 2 to 6 hours.

4. The process of claim 3 wherein the imidating agent is triloweralkyloxonium tetrafluoroborate.

5. The process of claim 4 wherein the imidating agent is triethyloxonium tetrafluoroborate.

6. The process of claim 3 wherein the imidating agent is phosphorous pentahalide.

7. The process of claim 6 wherein the imidating agent is phosphorous pentachloride.

8. A compound having the formula:
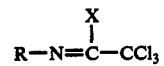
wherein R is 3-indolylmethyl; and X is loweralkoxy or halogen.
9. The compound of claim 8 wherein X is methoxy, ethoxy or chlorine.
* * * * *